United States Patent [19]

Gurmarnik

[11] Patent Number: 5,334,161
[45] Date of Patent: Aug. 2, 1994

[54] CATHETER WITH NEEDLE TRAP

[76] Inventor: Simon Gurmarnik, 38 Garrison Rd., #1, Brooklyne, Mass. 02146

[21] Appl. No.: 64,215

[22] Filed: May 21, 1993

[51] Int. Cl.⁵ ............................................... A61M 5/18
[52] U.S. Cl. .................. 604/164; 604/169; 604/198
[58] Field of Search ............... 604/117, 162, 165, 167, 604/169, 198, 248, 263

[56] References Cited

U.S. PATENT DOCUMENTS

| | | | |
|---|---|---|---|
| 2,091,438 | 8/1938 | Epstein | 604/117 |
| 3,766,916 | 10/1973 | Moorehead et al. | 604/167 |
| 4,447,235 | 5/1984 | Clarke | 604/169 |
| 4,863,430 | 9/1989 | Klyce et al. | 604/164 |
| 5,183,468 | 2/1993 | McLees | 604/164 |
| 5,195,974 | 3/1993 | Hardy | 604/164 |

FOREIGN PATENT DOCUMENTS 2088215 12/1981 United Kingdom ............... 604/167

*Primary Examiner*—John D. Yasko
*Assistant Examiner*—Anthony Gutowski
*Attorney, Agent, or Firm*—Ilya Zborovsky

[57] ABSTRACT

A device for IV therapy and the like has a needle and a hollow catheter for inserting the needle and provided with a tip and a rear end having a first inlet with a membrane for introducing the needle and a second separate needle for connecting a syringe or IV tubing, to prevent a blood backflow when the needle is removed. The device also has a needle tip trap in which the needle tip is trapped when the needle is removed from the catheter.

8 Claims, 2 Drawing Sheets

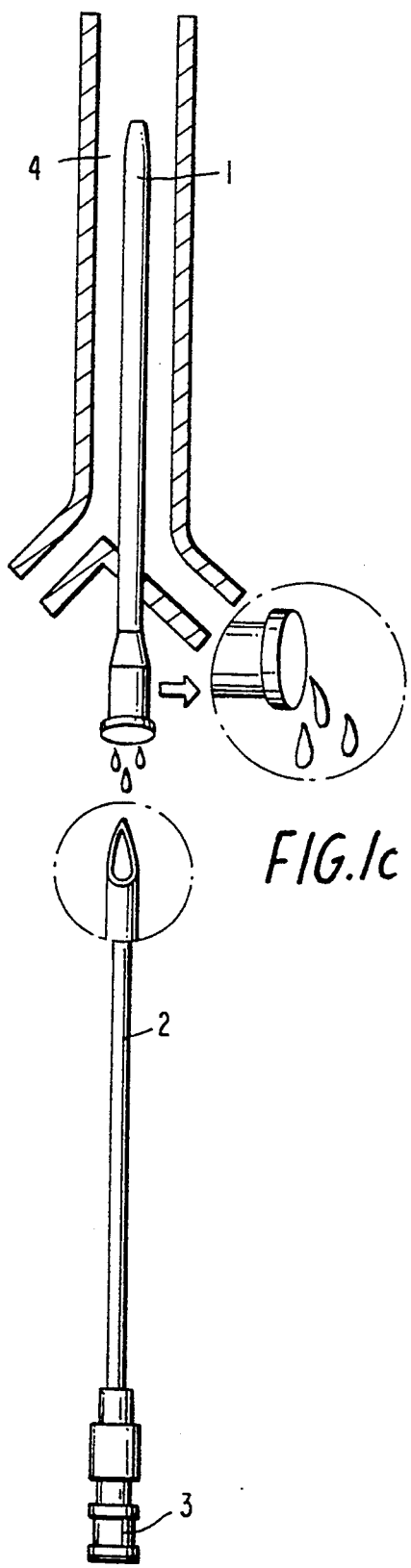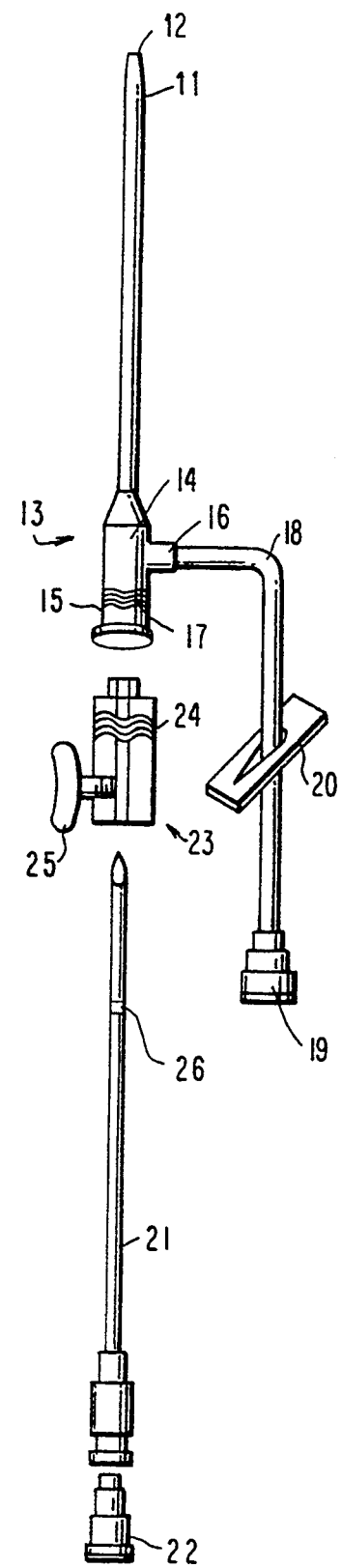
FIG. 1a PRIOR ART
FIG. 1b PRIOR ART
FIG. 1c
FIG. 2a

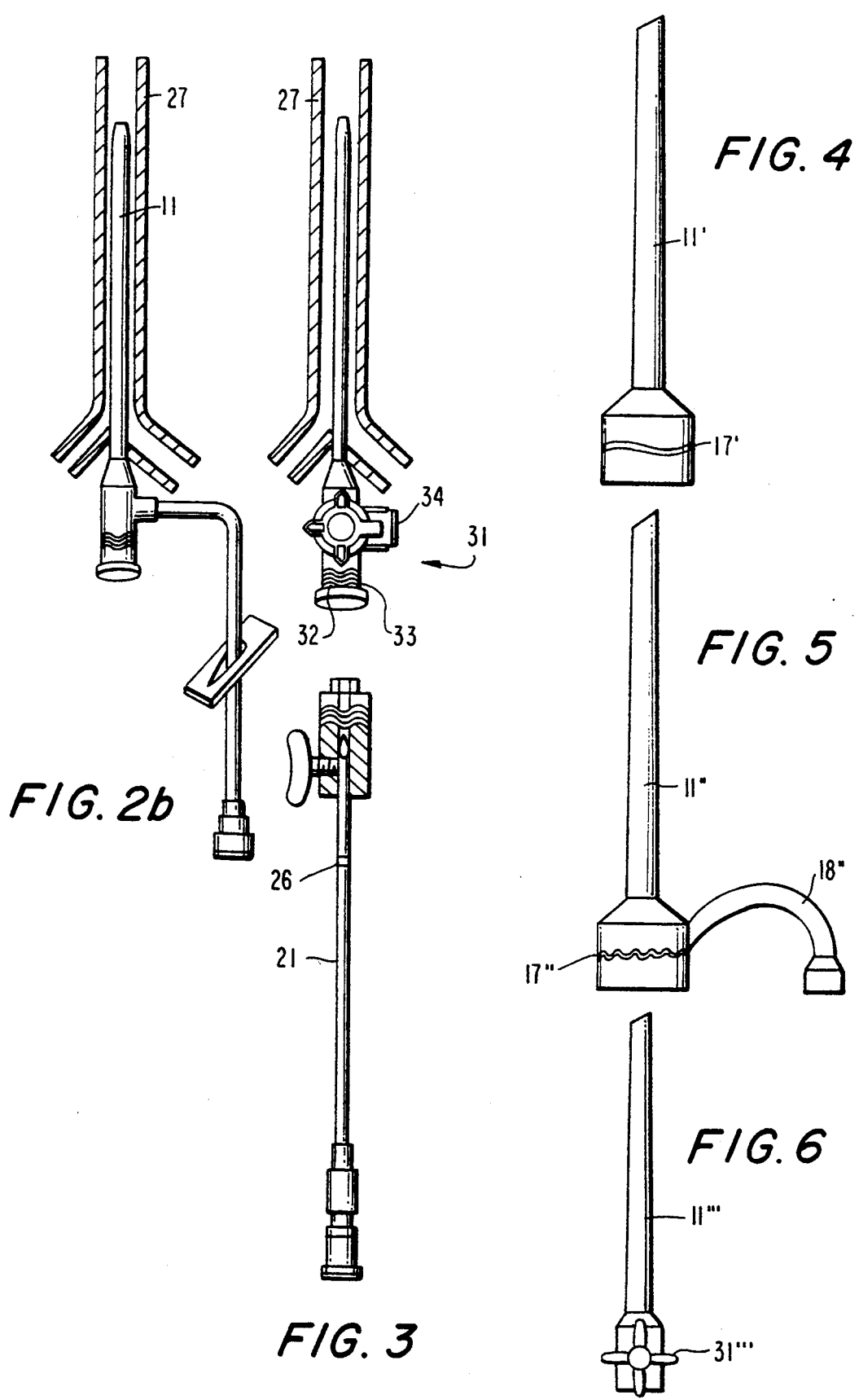

CATHETER WITH NEEDLE TRAP

BACKGROUND OF THE INVENTION

The present invention relates to devices for IV therapy and the like.

Devices of the above mentioned general type are known in the art. One of the known devices includes a plastic catheter 1, a hollow metal needle 2 with a sharp end, and an air filter 3 as shown in FIGS. 1a, 1b and 1c. In operation after the entire device is placed in the vein and blood appears in the chamber of the air filter 3, the metal needle 2 is removed leaving the catheter 1 in the vein 4. From this moment and until the connection is made with the syringe or IV tubing, the patient's blood is freely flowing from the lumen of the plastic catheter 1 and contaminates the field as shown in FIGS. 1b and 1c. At the same time, accidental stabbing of the operator by a sharp end of the metal needle 2 contaminated with the patient's blood is possible. It is to be understood that this can pose a grave danger for the operator since the patient's blood can contain for example HIV virus.

SUMMARY OF THE INVENTION

Accordingly, it is an object of the present invention to provide a device for IV therapy and the like, which avoids the disadvantages of the prior art.

In keeping with these objects and with others which will become apparent hereinafter, one feature of the present invention resides, briefly stated, in a device for IV therapy and the like, which has an elongated catheter and a needle, wherein the catheter has a tip and a rear end provided with two separate inlets including a first inlet having a membrane and adapted for introducing the needle through the first inlet and the membrane into the catheter and a second inlet which is separate from the first inlet and adapted for connection of a syringe or IV tubing thereto.

When the device is designed in accordance with the present invention, when the needle is removed from the catheter leaving it in the vein, blood is not flowing through and out of the catheter, and therefore no contamination of the field occurs.

In accordance with a further feature of the present invention, a trap for a needle tip is provided between the first inlet of the catheter and the needle in disassembled position, so that when in the assembled position the needle is withdrawn from the catheter its tip remains confined inside the trap and cannot stub the operator.

The novel features of the present invention are set forth in the appended claims. The invention itself, however, both as to its construction and its manner of operation will be best understood from the following description of preferred embodiments, which is accompanied by the following drawings.

BRIEF DESCRIPTION OF THE DRAWINGS

FIGS. 1a, 1b and 1c are views showing a device for IV therapy and the like in accordance with the prior art before use and when a needle is withdrawn from a catheter correspondingly;

FIGS. 2a and 2b are views showing a device for IV therapy and the like in accordance with the present invention before the use and when the needle is withdrawn from the catheter correspondingly;

FIG. 3 is a views showing the device for IV therapy in accordance with a further modification of the present invention; and FIGS. 4, 5, 6 show further modifications of the present invention.

DESCRIPTION OF PREFERRED EMBODIMENTS

A device for IV therapy and the like has a catheter which is preferably plastic and is identified as 11. The catheter is hollow and has an open tip 12 and a rear end 13. The rear end 13 is substantially T-shaped. One upper leg of it is connected with the body of the catheter. Another lower leg 15 extends downwardly. A third leg 16 extends to the right. The legs 15 and 16 form two inlets.

A membrane 17 is arranged in the leg 15 of the catheter. An extension 18 extends from the leg 16 and is provided with a connector 19 formed for example as a luer lock. A tubing clip 20 is arranged on the extension 18. As can be seen from the drawings, the point of connection of the leg 16 with the body of the catheter is located closer to the tip 12 of the catheter than the membrane 17.

The device further has a needle 21 composed preferably of metal and provided with an air filter 22. The device also has a needle trap 23 which is formed as a tube with an inner passage for the needle and has a membrane 24 and a wing screw 25. The needle 21 has a color mark 26. The above described construction is shown in FIGS. 2a and 2b.

The device shown in FIGS. 2a and 2b operates in the following manner.

The device is first inserted in a vein 27, and then the operator begins withdrawing the needle 21 from the catheter 11. The operator stops withdrawal when the tip of the needle is in the trap 23 and tightens the wing screw 25, thus immobilizing the sharp end of the needle within the needle trap. Then the needle 21 and the trap 23 are safely removed together from the arena preventing occurences of accidental stabbing. The membrane 17 prevents back flow of blood when the metal needle is withdrawn, yet the catheter is ready to be used for IV therapy through the extension 18, and no contamination of the field can occur.

The device in accordance with the embodiment shown in FIG. 3 operates substantially the same way. It somewhat differs from the embodiment of FIGS. 2a and 2b structurally. In particular, instead of the T-connection 13 and the extension 18, the catheter is provided with a three-way stopcock valve. The valve is identified as 31 and has an inlet 32 provided with a membrane 33 for introducing a needle, and an inlet 34 for connecting a syringe or IV tubing. The device is also provided with a similar trap for a tip of the needle. By means of the valve the inlet 32 is open for introducing the needle and then closed after withdrawing the needle. The inlet 34 is first closed and then open for connecting to the syringe or IV tubing and operating the latter.

The trap 23 can be connected to the catheter by interengaging projection and opening, or in any other acceptable way.

In the embodiments shown I in FIGS. 4, 5, 6 the needles are not shown. The catheter of FIG. 4 is identified as 11' and has a membrane 17'. The catheter of FIG. 5 has a membrane 1 and an extension 18" and is identified as a whole with 11". The catheter of FIG. 6 is identified as 11''' and has a three-way stopcock valve.

The present invention is not limited to the details shown since various modifications and structural changes are possible without departing in any way from the spirit of the invention.

I claim:

1. A device for IV therapy and the like, comprising a hollow catheter having a tip and a rear end; a needle insertable into said catheter, said rear end of said catheter having a first inlet provided with a membrane and formed so that said needle can be inserted through said first inlet and said membrane into said catheter, and a second separate inlet formed so that a syringe or an IV tubing can be inserted through said second inlet into said catheter; and a trap for a tip of said needle when said needle is withdrawn from said catheter so that the tip of the needle remains enclosed by and obstructed within said trap, said trap having a passage through which said needle moves and means for blocking said tip of said needle inside said passage and including a screw which is screwable through a wall of said trap so as to partially extend into said passage and clamp said tip of said needle in the latter.

2. A device as defined in claim 1, wherein said rear end has a T-shaped provided with a first leg connected with said catheter, another leg forming said first inlet and a further leg forming said second inlet.

3. A device as defined in claim 1; and further comprising a tubular extension having one end connected with said second inlet and another end connectable with the syringe or IV tubing.

4. A device as defined in claim 3, wherein said another end of said extension is provided with a luer lock.

5. A device as defined in claim 3, wherein said extension is provided with a tubing clip.

6. A device as defined in claim 1; and further comprising a 3-way valve provided in said rear end of said catheter and operative for opening and closing said inlets.

7. A device as described in claim 1, wherein said trap is provided with a membrane.

8. A device as defined in claim 1, wherein said screw is formed as a wing screw.

* * * * *